US012661343B2

(12) United States Patent
Stuelsatz et al.

(10) Patent No.: US 12,661,343 B2
(45) Date of Patent: *Jun. 23, 2026

(54) COMPOSITIONS CONTAINING NICOTINAMIDE AND VITAMIN B6 AND METHODS OF USING SUCH COMPOSITIONS FOR PROMOTING MUSCLE GROWTH

(71) Applicant: SOCIETE DES PRODUITS NESTLE S.A., Vevey (CH)

(72) Inventors: Pascal Stuelsatz, Crissier (CH); Jerome Feige, Crissier (CH); Joris Michaud, Lausanne (CH); Sara Ancel, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 422 days.

This patent is subject to a terminal disclaimer.

(21) Appl. No.: 18/250,893

(22) PCT Filed: Oct. 29, 2021

(86) PCT No.: PCT/EP2021/080141
§ 371 (c)(1),
(2) Date: Apr. 27, 2023

(87) PCT Pub. No.: WO2022/090473
PCT Pub. Date: May 5, 2022

(65) Prior Publication Data
US 2023/0390264 A1 Dec. 7, 2023

(30) Foreign Application Priority Data

Oct. 30, 2020 (EP) ..................................... 20204861

(51) Int. Cl.
| | |
|---|---|
| *C07D 213/82* | (2006.01) |
| *A61K 31/4415* | (2006.01) |
| *A61K 31/455* | (2006.01) |
| *A61P 21/00* | (2006.01) |
| *C07D 213/67* | (2006.01) |

(52) U.S. Cl.
CPC ........ *A61K 31/4415* (2013.01); *A61K 31/455* (2013.01); *A61P 21/00* (2018.01)

(58) Field of Classification Search
CPC ............... C07D 213/82; C07D 213/67; A61K 31/4415; A61K 31/455; A61P 21/00
See application file for complete search history.

(56) References Cited

U.S. PATENT DOCUMENTS

| | | | |
|---|---|---|---|
| 2012/0288588 A1 | 11/2012 | Barron | |
| 2023/0390262 A1* | 12/2023 | Stuelsatz | ................ A61P 21/00 |
| 2023/0390263 A1* | 12/2023 | Stuelsatz | ............ A61K 31/4415 |
| 2023/0398104 A1* | 12/2023 | Stuelsatz | ............ A61K 31/4415 |
| 2025/0186418 A1* | 6/2025 | Stuelsatz | ................ A61P 21/00 |

FOREIGN PATENT DOCUMENTS

| | | |
|---|---|---|
| AT | 513274 | 3/2014 |
| CN | 103860577 A | 6/2014 |
| CN | 107114800 | 9/2017 |
| CN | 109588709 | 4/2019 |
| RU | 2552006 C1 | 6/2015 |
| WO | 2005102301 | 11/2005 |
| WO | 2013056048 | 4/2013 |
| WO | 2013144268 A1 | 10/2013 |
| WO | 2018158234 A1 | 9/2018 |

OTHER PUBLICATIONS

Guo et al. "Nicotinamide protects against skeletal muscle atrophy in streptozotocin-induced diabetic mice" Archives of Physiology and Biochemistry, 2019, vol. 125, No. 5, pp. 470-477.
Suidasari et al. "Dietary vitamin B6 modulates the gene expression of myokines, Nrf2-related factors, myogenin and HSP60 in the skeletal muscle of rats" Experimental and Therapeutic Medicine, 2017, vol. 14, pp. 3239-3246.
Olguín, "Regulation of Pax7 Protein Levels by Caspase-3 and Proteasome Activity in Differentiating Myoblasts", Biological Research, vol. 44, Issue No. 4, 2011, pp. 323-327.
Vengerovsky, "Pharmacological Incompatibility", Scientific and Educational Process: Methodical Seminar, 2003, pp. 49-56.
Sedov et al., "Parametric Analysis of Regenerative Tissue Model Under Harmonic Exercise", Department of Energy, Engineering, Mechanics and Control Processes, 2015, pp. 506-509.
Krasnyuk et al., "Technological Drug Forms", 2nd Edition, Pharmaceutical Technology, 2006, p. 6.
Tentsova et al., "Modern Biopharmaceutical Aspects Substances", Pharmacy, vol. 7, 2012, pp. 1-14.
Kharkevich, "Pharmacology", 10th Edition, 2010, pp. 1-2 and 73.
Pilat et al., "Biologically Active Nutritional Supplements" 2002, pp. 94-96 and 122.
Kharkevich, "Pharmacology", 9th Edition, 2006, pp. 66-67.
Dunaev, "Solutions. Titration", 4th Edition, Workshop on Obsheichemia, 2005, p. 33.
Russian Office Action for Appl No. 2023110787/04 dated Mar. 7, 2025, 23 pages.
Shilyaev et al., "Current Approaches to Vitamin Therapy in Children of Early Childhood Period", 2007, 8 Pages.

(Continued)

*Primary Examiner* — Brenda L Coleman
(74) *Attorney, Agent, or Firm* — K&L Gates LLP

(57) ABSTRACT

A composition contains Nicotinamide and Vitamin B6, for example pyridoxine. The composition may be an oral nutritional composition, for example an infant formula, a follow up formula, a nutritional supplement, an oral nutritional supplement, a food product. The composition can be administered to an individual in need thereof for promoting muscle growth and/or for maintaining and/or increasing muscle function and/or muscle mass in infants and children. For example, the composition can be useful for increasing muscle function and/or muscle mass by modulating muscle stem cells.

16 Claims, 7 Drawing Sheets

(56) References Cited

OTHER PUBLICATIONS

Enoka et al., "Muscle Function: Strength, Speed, and Fatigability",
Muscle and Exercise Physiology, 2019, pp. 129-157.
Russian Office Action for Appl No. 2023110787/04 dated Aug. 15,
2025, 18 pages.

* cited by examiner

A

B

A

B

A

B

A

B

A)

B)

A)

B)

COMPOSITIONS CONTAINING NICOTINAMIDE AND VITAMIN B6 AND METHODS OF USING SUCH COMPOSITIONS FOR PROMOTING MUSCLE GROWTH

CROSS REFERENCE TO RELATED APPLICATIONS

The present application is a National Stage of International Application No. PCT/EP2021/080141, filed on Oct. 29, 2021, which claims priority to European Patent Application No. 20204861.7, filed on Oct. 30, 2020, the entire contents of which are being incorporated herein by reference.

TECHNICAL FIELD

The present disclosure generally relates to compositions containing Nicotinamide and Vitamin B6 and also relates to methods of preparing and using such compositions. The composition may be an oral nutritional composition, for example an infant formula, a follow up formula, a nutritional supplement, an oral nutritional supplement, a food product, a food for special medical purpose (FSMP). The composition can be administered for promoting muscle growth, preventing suboptimal muscle growth and/or for increasing muscle function and/or muscle mass in infants and children, for example to an individual in need thereof. In particular, promoting muscle growth and/or preventing suboptimal muscle growth in infants and children may be achieved by administering the composition according to the present invention and thereby increasing muscle function and/or muscle mass by modulating muscle stem cells function.

BACKGROUND

Skeletal muscles contain a population of muscle stem cells also known as satellite cells. These non-proliferative, quiescent muscle stem cells, can be identified by their distinct location between the muscle fiber sarcolemma and basal lamina, a high nuclear-to-cytoplasmic volume ratio, few organelles (e.g. ribosomes, endoplasmic reticulum, mitochondria, golgi complexes), small nuclear size, and a large quantity of nuclear heterochromatin relative to myonuclei. When activated muscle stem cells have an increased number of caveolae, cytoplasmic organelles, and decreased levels of heterochromatin.

These muscle satellite cells are involved in the regeneration following injury or disease as well as normal growth of muscle. Especially, muscle growth in young children depends on the activity of the muscle stem cells, which are responsible for the production of new myonuclei during postnatal muscle growth (Fiorotto et al., 2009; Davis et al., 2018). The functional need for a high muscle stem cell activity to support postnatal muscle growth has been clearly demonstrated in different animal models, and if their function is compromised this result in a proportional impairment of muscle growth (Kawano et al., 2008; Kuang et al., 2006).

To participate to muscle growth, muscle stem cells must exit the state of quiescence and become active, proliferate and commit to myogenic differentiation. Muscle stem cells express genetic markers at different stages of myogenesis and proliferation. Pax7 and Pax3 are considered to be satellite cell markers. For example, activated satellite cells expressing low levels of Pax7 are more committed to differentiation, whereas high levels of Pax7 are related to cells less prone to differentiate and have more undifferentiated stemness characteristics. Activation and the induction of myogenesis is typically regulated by myogenic regulatory factors such as MyoD, Myf5, myogenin and MRF4. Negative regulation by myostatin and TGFb inhibits the differentiation of satellite cells (Almeida et al., 2016).

These muscle stem cells are a potential target to enhance muscle growth in both healthy and diseased conditions.

Therefore, there is a significant need to identify compounds, compositions and methods, which modulate muscle stem cells directly for maintaining muscle health and promoting muscle growth. Such compounds, compositions and methods of treatment may help subjects to develop and maintain a proper muscle growth during infancy and childhood by facilitating maintenance of or increasing muscle function and/or muscle mass.

SUMMARY OF THE INVENTION

Healthy postnatal muscle growth primarily results from muscle hypertrophy through the increase in muscle fiber length and girth. Indeed, in mammals, the number of muscle fiber is determined before birth and except in pathological conditions, there is no significant change in postnatal fiber number. Muscle growth happens through hypertrophy when the protein synthesis rate is higher than the protein degradation rate which results in a net muscle protein gain. This is typically regulated by anabolic hormonal signals such as growth hormone, insulin/IGF-1 and androgens, as well as anabolic nutritional signals where branched chain amino acids from dietary protein stimulates muscle protein synthesis through mTOR. However, a muscle fiber is a unique cell with multiple nuclei which is formed by the fusion of multiple single cells called myoblasts. —Muscle growth through anabolic signaling saturates when the amount of myogenic nuclei within a muscle fiber becomes limiting. —Muscle growth therefore becomes dependent on the capacity of adding new nuclei to myofibers which is conferred by satellite cells activation, proliferation and fusion to existing myofibers. This mechanism is particularly relevant during the intense period of muscle growth that takes place during the first years of life.

As set forth in the experimental examples disclosed later herein, the present inventors surprisingly identified Nicotinamide as an enhancer of both amplification and commitment of muscle stem cells and vitamin B6 as an enhancer of their commitment. The present inventors also surprisingly found that the effect of Nicotinamide and pyridoxine when tested alone, was potentiated when cells were treated with a combination of these two compounds. This synergistic effect that is shown and described in FIG. 3 might be explained by the fact that Nicotinamide and vitamin B6 act differently on the muscle stem cells with Nicotinamide increasing mainly the amplification step (Pax7 cells) while vitamin B6 targeting specifically the commitment step (MyoD cells). This effect has been shown to be specific to vitamin B6 compared with other B vitamins (e.g B9). A composition comprising the combination was advantageous in maintaining stem cell function. In particular, a combination of Nicotinamide and pyridoxine, for example at specific concentrations and/or specific ratios thereof, unexpectedly showed a statistically significant synergistic association between the Nicotinamide and pyridoxine and the increase in muscle regeneration by promoting muscle stem cell function, thus suggesting a beneficial effect of these nutrients on promotion of muscle growth and/or prevention of suboptimal muscle growth, especially by maintaining and/or increasing muscle function and/or muscle mass in an individual in need thereof, especially an infant or child.

In an aspect of the present disclosure, a composition comprises a combination of Nicotinamide and pyridoxine (Vitamin B6) preferably an amount of the combination that is therapeutically effective for at least one of the physiological benefits disclosed herein.

In an embodiment, the composition comprises vitamin B6 in an amount of a daily dosage of 1.0-200 mg of vitamin B6/day, for example 1.0-25.0 mg of vitamin B6/day, for example 1.0-15.0 mg of vitamin B6/day, for example 1.0-10 mg of vitamin B6/day, for example 1.0-7.0 mg of vitamin B6/day.

In an embodiment, the composition comprises Nicotinamide in an amount of about 0.001 mg/day to about 2000 mg/day, for example about 0.001 mg/day to about 700 mg/day, for example about 1 mg/day to about 500 mg/day, for example of about 1 mg/day to about 350 mg/day, for example about 1 mg/day to about 220 mg/day. However, in any given case, the amount of compound administered will depend on such factors as the solubility of the active component, the formulation used, subject condition (such as weight), and/or the route of administration. For example, the daily doses of Vitamin B6 or Nicotinamide disclosed above are non-limiting and, in some embodiments, may be different.

In an embodiment, the composition is in a form of a solid powder, a powdered stick, a capsule or a solution. The composition can be a food supplement, a medical food, a nutritional composition, for example an infant formula or a growing up milk.

In another aspect of the present disclosure, a method of preparing the composition is provided. The method can comprise combining Vitamin B6 (for example Pyridoxine) and Nicotinamide, and preferably an amount of the resultant combination that is therapeutically effective for at least one of the physiological benefits disclosed herein.

In another aspect of the present disclosure, a nutritional composition or nutritional supplement comprises a therapeutically effective amount of any of the compositions disclosed herein. In an embodiment, the nutritional composition or nutritional supplement is an oral nutritional supplement (ONS). The nutritional composition or supplement can be in a form of a solid powder, a powdered stick, a capsule, or a solution. In an embodiment, the nutritional supplement comprises vitamin B6 in a daily dosage of 1.0-25 mg of vitamin B6/The nutritional supplement can comprise Nicotinamide in a total daily dosage 0.001 mg/day to about 1000 mg/day, preferably about 1 mg/day to about 500 mg/day.

In an embodiment, the food product further comprises one or more additional ingredients, for example a lipid, a protein, a carbohydrate, a vitamin, a mineral, or any combination thereof.

In another aspect of the present disclosure, a kit comprises a therapeutically effective amount of any of the compositions disclosed herein. In an embodiment, the kit is configured for oral administration of the composition. For example, the kit can comprise at least two capsules in which a first capsule comprises the vitamin B6 and a second capsule comprises Nicotinamide. In an embodiment, the kit comprises vitamin B6 in the first capsule in a daily dosage of 1.0-25 mg of the vitamin B6. In an embodiment, the kit comprises the Nicotinamide in the second capsule in a total daily dosage of 0.001 mg/day to about 2000 mg/day, preferably about 1 mg/day to about 500 mg/day.

In another aspect of the present disclosure, a method of promoting muscle growth, of preventing suboptimal muscle growth and/or of increasing muscle function and/or muscle mass. The method comprises administering to an individual in need thereof a therapeutically effective amount of a combination of vitamin B6 and Nicotinamide and/or derivatives. In an embodiment, the administration is by oral administration. In another embodiment, the administration is by intravenous administration. The present invention also relates to a method for increasing muscle function and/or muscle mass in a subject. In one embodiment, the invention also relates to a method for increasing muscle function and/or muscle mass in a subject by modulating muscle stem cells. In another embodiment, the present invention also relates to a method for promoting muscle growth and/or preventing sub optimal muscle growth (by increasing muscle function and/or muscle mass) in a subject.

In one embodiment, the subject is a human subject.

In one embodiment, the human subject is an infant or a child.

In one embodiment, the subject is a companion animal, preferably a dog.

Human Skeletal Muscle Myoblasts were purchased from Lonza (https://bioscience.lonza.com). These cells were isolated from the upper arm or leg muscle tissue of normal donors and used after the second passage. Several donors were tested to ensure cell viability and purity before selecting the final donors, which are a 20-year-old Caucasian female (refer thereafter as Donor 1), a 36-year-old Caucasian female (refer thereafter as Donor 2) and a 18-year-old Caucasian male (refer thereafter as Donor 3). Human primary myoblasts were seeded in 384 well plates at a density of 1'000 cells per well in skeletal muscle growth medium (SKM-M, AMSbio). For treatment, compounds were directly added to the myoblast cultures 16 hours after initial plating.

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. *, , *, **** indicates difference from the control, One-way ANOVA, with $p<0.05$, $p<0.01$, $p<0.001$, $p<0.0001$, respectively. Data are presented as Mean+/− SEM.

Figure 1:
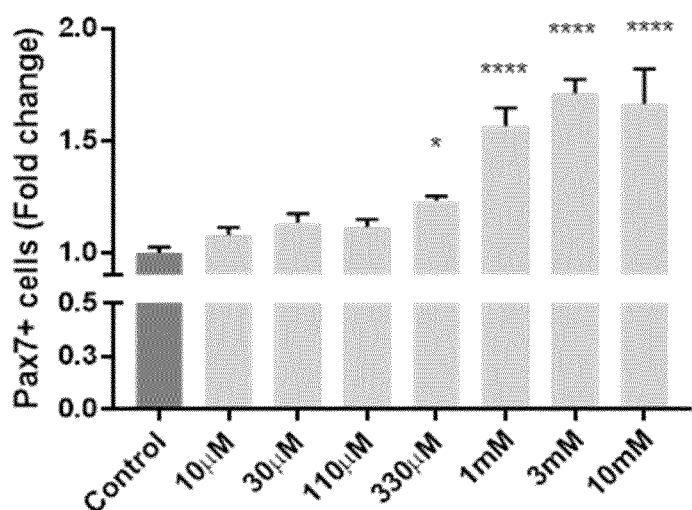
FIGS. 1 to 5—Myogenic amplification and commitment of muscle stem cells
Figure 1:
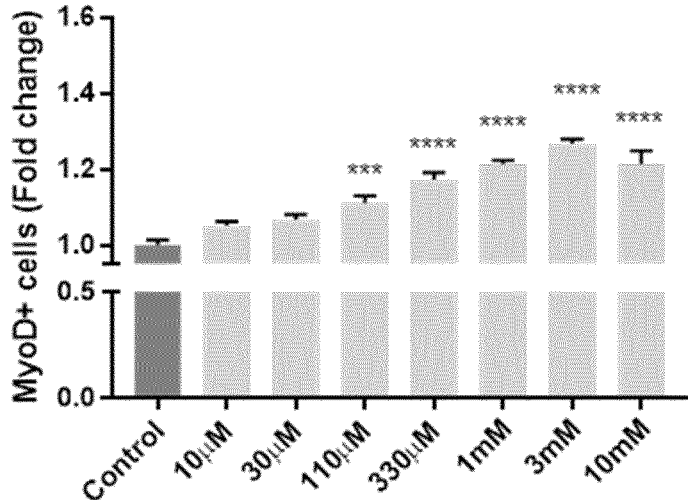

FIG. 1: In vitro dose response of Nicotinamide. Data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells.

Figure 2:
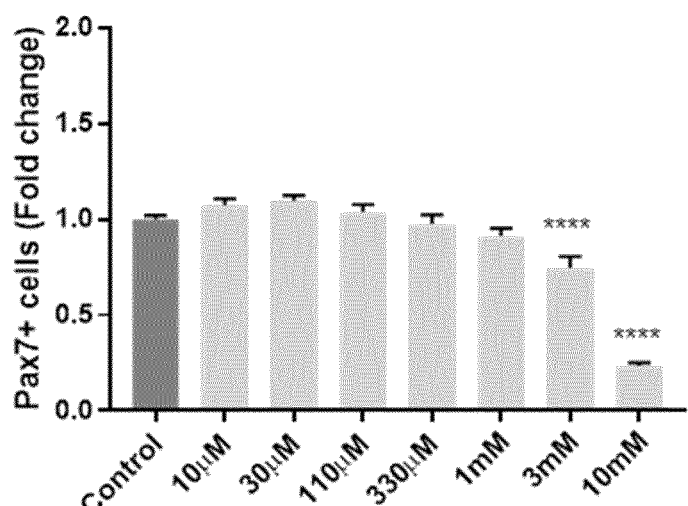
Figure 2:
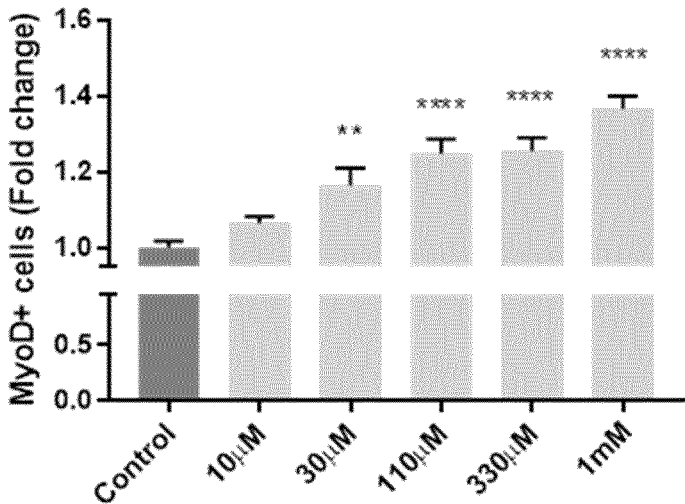

FIG. 2: In vitro dose response of Pyridoxine (B6). Data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells.

Figure 3:
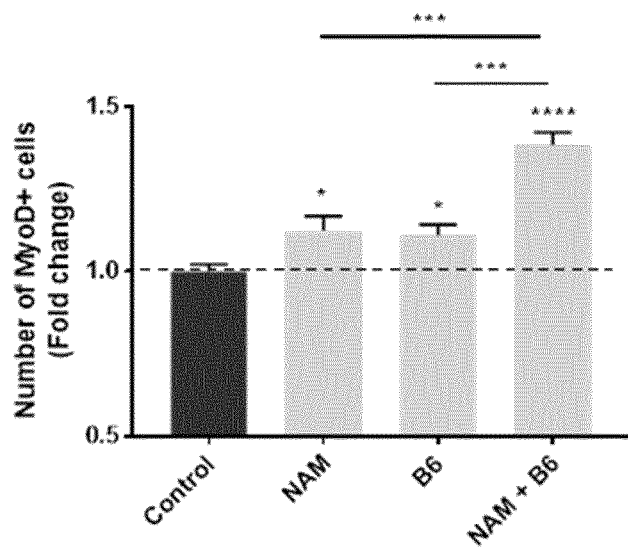
Figure 3:
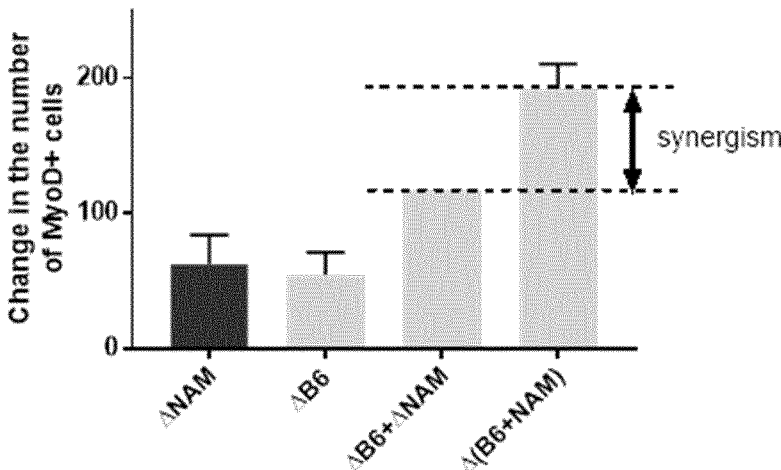

FIG. 3: Synergistic effect of Nicotinamide (NAM) and pyridoxine (B6). The effect of nicotinamide and pyridoxine alone or combined on the MyoD+ cells was assessed on Human primary myoblasts from donor 3. For each condition, the number of MyoD+ cells was normalized to the number of MyoD+ cells in the control condition (DMSO 1%). FIG. 3A represents the number of MyoD+ cells normalized to the control condition. FIG. 3B represents the change in MyoD+ cell number compared to the control condition (DMSO 1%). ΔB6 or ΔNAM refers to the change from the control condition with B6 or NAM treatment, respectively. ΔB6+ΔNAM refers to the theoretical sum of the effects of B6 and NAM measured separately. Δ(B6+NAM) refers to the experimental effects of a combined treatment with B6 and NAM. A statistically significant synergistic effect between the nicotinamide and pyridoxine has been observed by applying a linear regression model (interaction term, $p=0.05$).

Figure 4:
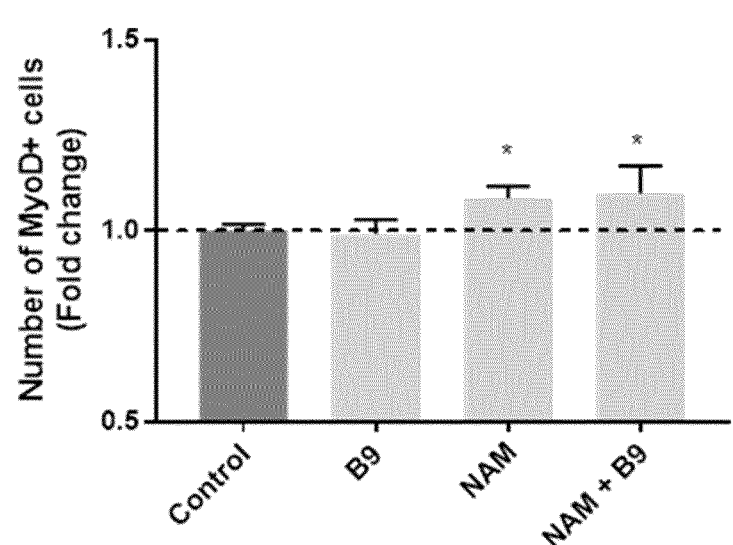
Figure 4:
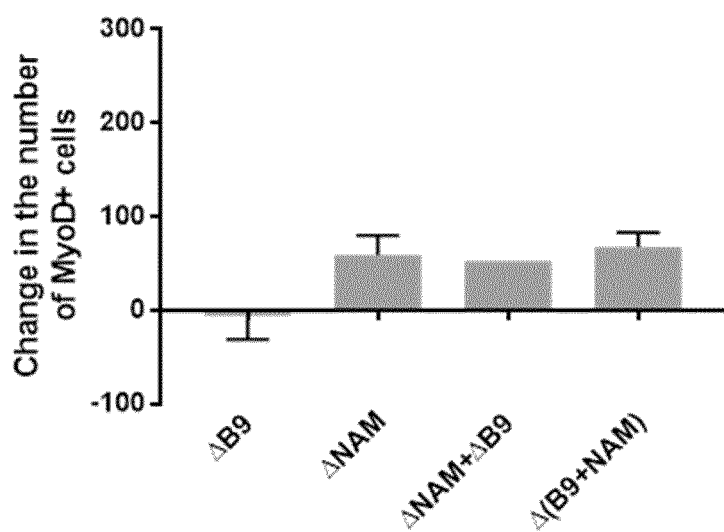

FIG. 4 Combination of Nicotinamide (NAM) with vitamin B9. The effect of nicotinamide and vitamin B9 alone or combined on the MyoD+ cells was assessed on Human primary myoblasts from donor 3. For each condition, the number of MyoD+ cells was normalized to the number of MyoD+ cells in the control condition (DMSO 1%). FIG. 4A represents the number of MyoD+ cells normalized to the control condition. FIG. 4B represents the change in MyoD+ cell number compared to the control condition (DMSO 1%).

Figure 5:
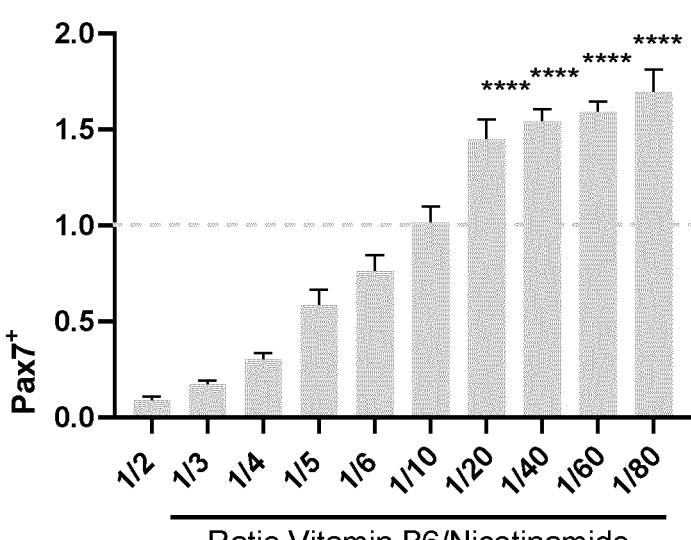

FIG. 5 represents the number of Pax7+ cells for different ratios between Pyridoxine and Nicotinamide (ratio Vitamin B6/NAM).

Figure 6:
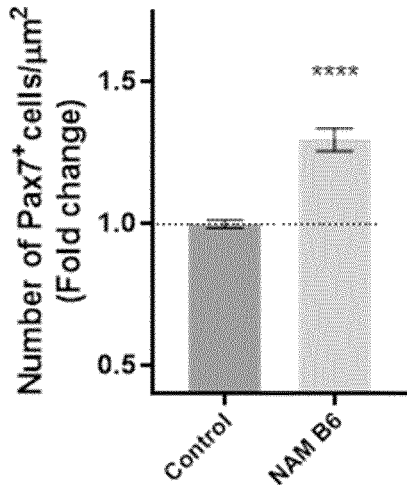
Figure 6:
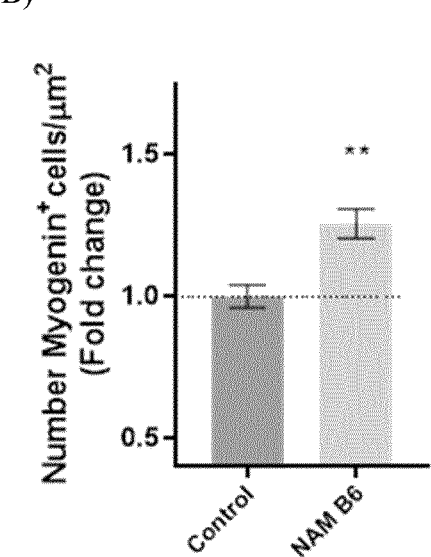

FIG. 6: In vivo effect of the combination of nicotinamide (NAM) and pyridoxine (B6) on muscle stem cells function FIG. 6 represents early phase of expansion and subsequent phase of myogenic differentiation of Muscle Stem Cells, evaluated by counting the number of Pax7+ cells (FIG. 6A) and Myogenin+ cells (FIG. 6B), respectively. Data are expressed as number of cells per arear of injured muscle and expressed as a fold change compared to the control condition. *, , *, **** indicates difference from the control, One-way ANOVA, with $p<0.05$, $p<0.01$, $p<0.001$, $p<0.0001$, respectively. Data are presented as Mean+/−SEM.

Figure 7:
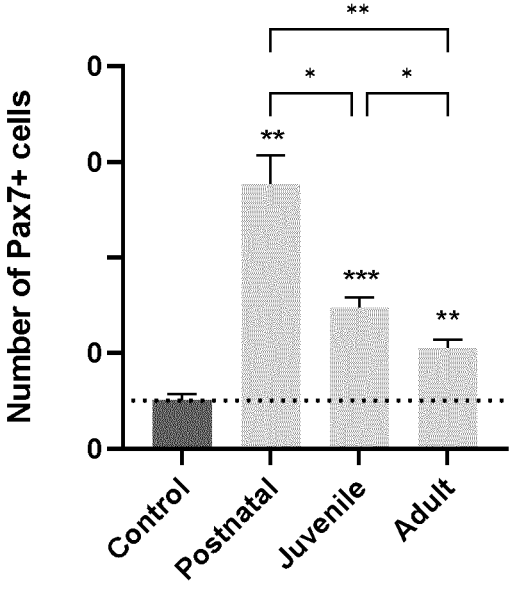
Figure 7:
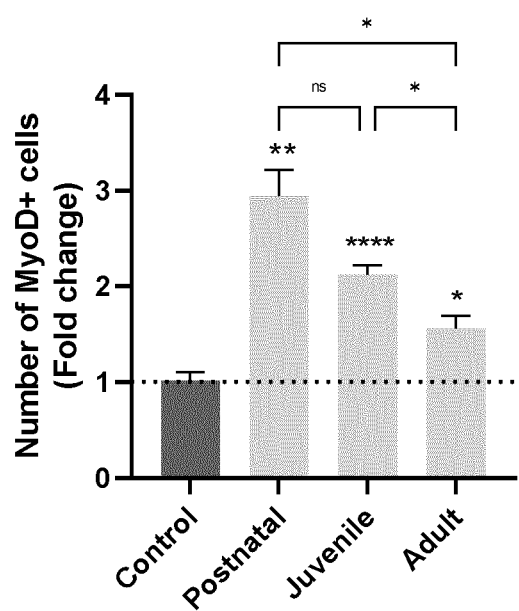

FIG. 7: effect of the combination of nicotinamide (NAM) and pyridoxine (B6) on amplification and commitment of Muscle Stem Cells isolated at different ages after birth. For each age group, postnatal (4-day-old), juvenile (3-week-old) and adult (26-week-old), the total number of Pax7+ or MyoD+ cells in the conditions treated with NAM/B6 was normalized to the number of cells in the respective control conditions and expressed as a fold change compared to the control condition (DMSO 1%). FIG. 7A represents the number of Pax7+ cells and FIG. 7B represents the number of MyoD+ cells.

DETAILED DESCRIPTION

Definitions

The term "infant" means a child under the age of 12 months. The expression "young child" or "toddler" means a child aged between one and less than three years. The expression "child" means a between three and seven years of age.

A "preterm" or "premature" means an infant or young child who was not born at term. Generally, it refers to an infant or young child born prior 37 weeks of gestation.

The expression "nutritional composition" means a composition which nourishes a subject. This nutritional composition is usually to be taken orally or intravenously, and it usually includes a lipid or fat source and a protein source. Non limiting examples of nutritional composition according to the present invention are selected in the group consisting of: infant formula (for example, follow up formula), baby food, infant cereal composition, growing up milk, fortifier and nutritional supplement (for example paediatric supplement).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex *Alimentarius* (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for fortifying or mixing with human milk, infant formula, growing-up milk or human breast milk fortified with other nutrients. Accordingly, the fortifier of the present invention can be administered after dissolution in human breast milk, in infant formula, in growing-up milk or in human breast milk fortified with other nutrients or otherwise it can be administered as a stand-alone composition. When administered as a stand-alone composition, the milk fortifier of the present invention can be also identified as being a "supplement". In one embodiment, the milk fortifier of the present invention is a supplement.

The term "nutritional supplement" refers to a product which is intended to supplement the general diet of a subject.

The term "paediatric supplement" refers to a product which is intended to supplement the general diet of a infant, a young child or a child.

The expression "weaning period" means the period during which the mother's milk is substituted by other food in the diet of an infant or young child.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example, "at least one of Nicotinamide or Vitamin B6" should be interpreted as "Nicotinamide," or "Vitamin B6," or "both Nicotinamide and Vitamin B6."

Where used herein, the terms "example" and "such as," particularly when followed by a listing of terms, are merely exemplary and illustrative and should not be deemed to be exclusive or comprehensive.

A "subject" or "individual" is a mammal, preferably a human, for example an infant, young child or child. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form," as used herein, refers to physically discrete units suitable as unitary dosages for human and animal subjects, each unit containing a predetermined quantity of the composition disclosed herein in an amount sufficient to produce the desired effect, in association with a therapeutically effective diluent, carrier or vehicle. The specifications for the unit dosage form depend on the particular compounds employed, the effect to be achieved, and the pharmacodynamics associated with each compound in the host.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

The term "food for special medical purpose (FSMP)" refers to formula foods specially processed and prepared in order to meet special needs for nutrient or diet of those suffering from food intake restriction, disorder of digestive absorption, disorder of metabolic or certain diseases. Such foods shall be used alone or together with other foods under the guidance of a doctor or clinical nutritionist. FSMP is special dietary food, not medicine, but not ordinarily eaten by normal people. It is specially developed by clinicians and nutritionists based on scientific facts after extensive medical research.

The term "oral nutritional supplement (ONS)" refers to sterile liquids, semi-solids or powders, which provide macro and micronutrients. They are widely used within the acute and community health settings for individuals who are unable to meet their nutritional requirements through oral diet alone.

As used herein, "vitamin B6" can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP. [2] Pyridoxine 5'-phosphate oxidase is dependent on flavin mononucleotide (FMN) as a cofactor produced from riboflavin (vitamin B2).

Within the context of the present invention, the term "niacinamide" is to be intended as a synonym of nicotinamide.

"Mobility" is the ability to move independently and safely from one place to another.

Muscle mass can be measured by CT (computerised tomography), DXA (Dual-energy X-ray absorptiometry), MRI (Magnetic Resonance Imaging) or D3 creatine dilution methods.

Muscle strength can be measured by handgrip strength (for example, using hand held dynamometry) or knee extensor strength (for example, using quadriceps torque measurement).

Physical performance can be measured by gait speed, SPPB, 400 m walk test, time up and go test, or stair climbing test.

The D3-creatine dilution method is another approach to measure muscle mass. This method is becoming more widely accepted as a robust standard and potentially a future alternative to DXA. The D3-creatine dilution method has been described previously e.g. in Clark et al. (2014) "Total body skeletal muscle mass: estimation by creatine (methyl-d3) dilution in humans" J Appl Physiol (1985). 2014 Jun. 15,116(12):1605-13 and Stimpson et al. (2013) "Longitudinal changes in total body creatine pool size and skeletal muscle mass using the D3-creatine dilution method" J Cachexia Sarcopenia Muscle. June 25.

Embodiments

An aspect of the present disclosure is a composition comprising Nicotinamide and Vitamin B6. The composition comprising the Nicotinamide and Vitamin B6 is advantageous in promoting muscle growth and/or preventing suboptimal muscle growth or in increasing muscle function and/or muscle mass. In one embodiment, the present invention provides for a composition comprising nicotinamide and pyridoxine.

Composition

Nicotinamide

Nicotinamide, also known as niacinamide or nicotinic acid amide, is the water-soluble, active form of vitamin B3.

The nicotinamide can be administered in an amount of about 0.001 mg/day to about 2000 mg/day, more preferably about 1 mg/day to about 750 mg/day, even more preferably about 1 mg/day to about 500 mg/day, most preferably about 1 mg/day to about 250 mg/day, for example about 1 mg/day to about 100 mg/day, about 1 mg/day to about 75 mg/day, about 1 mg/day to about 50 mg/day, about 1 mg/day to about 25 mg/day, or about 1 mg/day to about 10 mg/day. Of course, the daily dose can be administered in portions at various hours of the day. However, in any given case, the amount of compound administered will depend on such factors as the solubility of the active component, the formulation used, subject condition (such as weight), and/or the route of administration. For example, the daily doses of nicotinamide disclosed above are non-limiting and, in some embodiments, may be different; in particular, the compositions disclosed herein can be utilized as an acute care food for special medical purposes (FSMP) and contain up to about 2.0 g nicotinamide/day.

Vitamin B6

In an embodiment, vitamin B6 can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP. [2] Pyridoxine 5'-phosphate oxidase is dependent on flavin mononucleotide (FMN) as a cofactor produced from riboflavin (vitamin B2).

Pyridoxine is the 4-methanol form of vitamin B6, an important water-soluble vitamin that is naturally present in many foods.

In one embodiment, Vitamin B6 is pyridoxine.

In an embodiment, Vitamin B6 can be administered in a daily dosage of 1.0-25.0 mg of the vitamin B6/day.

In an embodiment, the combination is particularly effective, in particular on both amplification and commitment of muscle cells, when the Vitamin B6:Nicotinamide are present in a ratio of from about 1:100 to about 1:9, preferably from about 1:80 to about 1:20, preferably from about 1:75 to about 1:25, more preferably from about 1:60 to about 1:30. In one embodiment, the Vitamin B6:Nicotinamide are present in a ratio of from about 1:45 to about 1:30.

In some embodiments, the composition comprising a combination of the Nicotinamide and Vitamin B6 is in the form of a nutritional composition.

The nutritional composition according to the invention can be for example an infant formula, a starter infant formula, a follow-on or follow-up formula, a growing-up milk, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

In some embodiments, the composition comprising a combination of the Nicotinamide and Vitamin B6 is in the form of a food product, food supplement, nutraceutical, food for special medical purpose (FSMP), nutritional supplement, dairy-based drink, low-volume liquid supplement or meal replacement beverage.

In some embodiments, the composition comprising a combination of the Nicotinamide and Vitamin B6 is in the form of a food additive or a medicament.

A food additive or a medicament may be in the form of tablets, capsules, pastilles or a liquid for example. Food additives or medicaments are preferably provided as sustained release formulations, allowing a constant supply of the active ingredients for prolonged times.

The composition may be selected from the group consisting of milk-powder based products; instant drinks; ready-to-drink formulations; nutritional powders; nutritional liquids; milk-based products, in particular yoghurts or ice cream; cereal products; beverages; water; coffee; cappucino; malt drinks; chocolate flavoured drinks; culinary products; soups; tablets; and/or syrups.

The composition may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and anti-microbials.

Further, the composition may contain an organic or inorganic carrier material suitable for oral or enteral administration as well as vitamins, minerals trace elements and other micronutrients in accordance with the recommendations of government bodies such as the USRDA.

The composition of the invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein and pea protein); mixtures of free amino acids; or combinations thereof. Milk proteins such as casein and whey, and soy proteins are particularly preferred.

If the composition includes a fat source, the fat source preferably provides 5% to 40% of the energy of the formula; for example, 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins and mixtures thereof.

Another aspect of the present disclosure is a kit comprising a therapeutically effective amount of any of the compositions disclosed herein. In an embodiment, the kit is configured for oral administration of the composition. For example, the kit can be in a form of two capsules, wherein the first capsule comprises the vitamin B6 and the second capsule comprises the Nicotinamide.

Another aspect of the present disclosure is a method of preparing the composition. The method can comprise combining a therapeutically effective amount of a combination of Nicotinamide and Vitamin B6, preferably an amount of the combination that is therapeutically effective for at least one of the physiological benefits disclosed herein.

Method of Treatment

It is to be appreciated that all references herein to treatment include curative, palliative and prophylactic treatment. The treatment of mammals, particularly humans, is preferred. Both human and veterinary treatments are within the scope of the invention.

In one embodiment of the present invention, the subject is an infant, young child or child. In a further embodiment, the subject is an infant or a young child. In a still further embodiment, the subject is an infant.

In an embodiment, the present invention provides a method for increasing muscle function and/or muscle mass and/or promote muscle growth in a subject. The method comprises administering to an individual in need thereof a therapeutically effective amount of any of the compositions disclosed herein. Non-limiting examples of the administration include oral administration. In an embodiment, the method comprises administering to an individual in need thereof a therapeutically effective amount of a combination of vitamin B6 and Nicotinamide.

In another embodiment, the method comprises administering to an individual in need thereof a therapeutically effective amount of a combination of an effective amount of vitamin B6 and Nicotinamide.

Although the composition for use in the invention can be administered alone, they will generally be administered in admixture with a pharmaceutical carrier, excipient or diluent, particularly for human therapy.

In a further embodiment of the invention, a compound or a composition of the invention may be used in a method of promoting muscle growth or maintaining and/or increasing muscle function and/or muscle mass in combination with a dietary intervention of high caloric, high protein, high carbohydrate, Vitamin B12 and/or Vitamin D supplementation, antioxidants, omega fatty acids, butyrate producers and/or polyphenols.

Within the context of the present invention, the expression "butyrate producer" indicate a substance or ingredient which, when administered to a subject, is able to deliver and/or stimulate the production of butyrate, for example in the gut of said subject. Not limiting examples of butyrate producers are: sodium butyrate, potassium butyrate and/or triglycerides containing butyrate such as for example those described in the International Patent Application WO2019/228851 of the same applicant.

In some embodiments, the composition comprising a combination of the Nicotinamide and Vitamin B6 is in a combined preparation for simultaneous, separate or sequential use, preferably simultaneous.

The term "combination", or terms "in combination", "used in combination with" or "combined preparation" as used herein may refer to the combined administration of two or more agents simultaneously, sequentially or separately.

The term "simultaneous" as used herein means that the agents are administered concurrently, i.e. at the same time.

The term "sequential" as used herein means that the agents are administered one after the other.

The term "separate" as used herein means that the agents are administered independently of each other but within a time interval that allows the agents to show a combined, preferably synergistic, effect. Thus, administration "separately" may permit one agent to be administered, for example, within 1 minute, 5 minutes or 10 minutes after the other.

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

In an embodiment, the method comprises administering to an individual in need thereof a therapeutically effective amount of a combination of vitamin B6 in a daily dosage of 1.0-25.0 mg of the vitamin B6/day and Nicotinamide in an amount of about 0.001 mg/day to about 1000 mg/day, preferably about 1 mg/day to about 500 mg/day.

In an embodiment, the combination is administered to the individual for a time period of at least one month; preferably at least two months, more preferably at least three, four, five or six months; most preferably for at least one year. During the time period, the combination can be administered to the individual at least one day per week; preferably at least two days per week, more preferably at least three, four, five or six days per week; most preferably seven days per week. The combination can be administered in a single dose per day or in multiple separate doses per day.

The above examples of administration do not require continuous daily administration with no interruptions. Instead, there may be some short breaks in the administration, such as a break of two to four days during the period of administration. The ideal duration of the administration of the composition can be determined by those of skill in the art.

Muscle Stem Cells

The term "muscle stem cell", as used herein, may refer to satellite cells, preferably satellite cells that are quiescent and are uncommitted.

Satellite cells are precursors to skeletal muscle cells. In adult muscle, satellite cells are generally quiescent, but can activate and undergo myogenesis in response to disease or mechanical strain such as injury or exercise. Satellite cells are also involved in the normal growth of muscle. Upon activation, satellite cells proliferate before undergoing myogenic differentiation to finally fuse with existing myofibers or to form new myofibers, depending on the magnitude of tissue trauma. In addition to generating differentiated myogenic progeny, at least some satellite cells can self-renew, thereby meeting the defining criteria of bona fide resident stem cells.

MyoD+ is a commitment marker that may be used to distinguish quiescent from committed satellite cells.

Muscle Function and Mass

The compounds, compositions, uses and methods disclosed herein may provide for the maintenance of or increase in muscle function and/or mass.

The term "muscle function" refers to the ability of a muscle to perform in a manner that does not negatively impact on the life of a subject, and encompasses parameters of muscle strength, muscle contraction, muscle endurance, muscle elasticity, ability of a muscle to resist muscle fatigue and/or physical activities of daily living such as walking up stairs, getting out of a chair and other activities of daily living.

Suitable tests for assessing muscle function include grip strength assessment using a dynamometer; one repeat maximum on leg press, chest press or leg extension; gait speed; 6 min walk test; time up and go; short physical performance battery; Fried frailty criteria; and stair climbing time assessments. Other suitable tests include muscle strength, endurance and time to fatigue.

Muscle mass (which may equate with muscle volume, muscle thickness or myofiber size) may be measured by dual-energy X-ray absorptiometry (DXA) or bioimpedance tests. Similarly, MRI may be used for assessing muscle volume and ultra-sound may be used for assessing muscle thickness and pennation angle.

"Muscle wasting" may be a reduction in muscle mass, for example to the stage where the muscle loss becomes debilitating. In one embodiment, the subject does not lose more than 10%, 5%, 4%, 3%, 2% or 1% of their muscle mass.

Preferably, the compounds, compositions, uses and methods disclosed herein provide for the maintenance of or increase in muscle mass.

The term "maintains" refers to a particular parameter, such as muscle function and/or mass, remaining substantially unchanged over a period of time (e.g. 5, 10, 15, 20, 25, 30, 40, 50 or more years).

In one embodiment, muscle mass increases by at least 1%, 2%, 3%, 4%, 5%, 10%, 15% or 20%.

In another embodiment, muscle mass increases by 1-2.5%, 1-5%, 1-10% or 1-20%.

Preferably, the muscle is skeletal muscle.

Muscle Growth

In one embodiment of the present invention, as a result of maintenance of or increase in muscle function and/or mass, the compounds, compositions, uses and methods disclosed herein provide for promotion of muscle growth and/or prevention of sub-optimal muscle growth in a subject, such as an infant, young child or child.

Within the context of the present invention the term "muscle growth" encompasses an increase of muscle mass, muscle volume and/or—muscle function, through time. Muscle growth may be evaluated by measuring muscle mass and/or function as above described.

Muscle growth can also be determined by an increase in muscle fiber number (hyperplasia) as well as an increase in muscle fiber size (hypertrophy).

Within the context of the present invention, the term "promoting" indicates a factor or a number of factors causing a certain process to occur.

Subject

In some embodiments, a subject is a human or non-human animal.

Non limiting examples of non-human animals include vertebrates, for example mammals, such as non-human primates (particularly higher primates), dogs, rodents (e.g. mice, rats or guinea pigs), pigs and cats. The non-human animal may be a companion animal.

Non-examples of non-human animal subjects are also avian, bovine, ovine or porcine animals. The present invention may also be useful in non-human animal subjects such as: avian, bovine, ovine or porcine animals, for optimizing meat production by increasing skeletal muscle mass and/or function.

Preferably, the subject is a human. In one embodiment, the subject is a human infant or young children. In one embodiment, the subject is a human preterm infant.

Preferably, the muscle functionality that can be improved by the methods disclosed herein comprises a characteristic selected from the group consisting of muscle strength, gait speed, and combinations thereof. Muscle function is typically defined as strength per unit of appendicular skeletal muscle mass or per muscle volume.

The individual can be at risk of a disorder or condition (e.g., impairment in one or more of muscle functionality, muscle performance, or muscle strength), in which case the effective amount of the composition is a prophylactically effective dose; or the individual can have a disorder or condition, in which case the effective amount of the composition is a therapeutically effective dose. In some embodiments, the methods comprise identifying the individual as having the condition or being at risk of the condition before the administration.

EXAMPLES

The following non-limiting examples support the unexpected effectiveness of a composition comprising Nicotinamide and vitamin B6 for increasing muscle function and/or muscle mass in a subject.

Example 1 Myogenic Amplification and
Commitment of Muscle Stem Cells

Material and Methods

Human primary myoblasts from different donors (donor 1, donor 2 or donor 3) were seeded in 384 well plates at a density of 1'000 cells per well in skeletal muscle growth medium (SKM-M, AMSbio). For treatment, compounds were directly added to the myoblast cultures 16 hours after initial plating.

All cultures were then grown for 96 hours. Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that do not express Pax7 but express MyoD. Image acquisition was performed using the ImageXpress (Molecular Devices) platform. Custom module analysis based on Multi-Wavelength Cell Scoring of the MetaXpress software was used for quantification. Additionally, several ratios between Pyridoxine and Nicotinamide (ratio Vitamin B6/NAM) ranging from 1:2 to 1:80 were tested and FIG. 5 represents the number of Pax7+ cells for these specific ratios in the same model.

*, , *, **** indicates difference from the control, One-way ANOVA, with $p < 0.05$, $p < 0.01$, $p < 0.001$, $p < 0.0001$, respectively. Data are presented as Mean+/−SEM Results Results are presented in FIGS. 1 to 5.

Data obtained from Human primary myoblasts from donors 1 and 2 were pooled (see FIG. 1). For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 1A represents the proportion of Pax7+ cells and FIG. 1B represents the proportion of MyoD+ cells. These data demonstrate that Nicotinamide promotes Muscle Stem Cell function by increasing the proportion of both amplifying (Pax7+) and differentiating (MyoD+) cells in a dose dependent manner.

Similarly, for Pyridoxine, data obtained from Human primary myoblasts from donors 1 and 2 were pooled. For each condition, the total number of cells was determined to evaluate compound toxicity, and the number of Pax7+ or MyoD+ cells was normalized to the total cell number in order to evaluate the proportion of this population and expressed as a fold change compared to the control condition (DMSO 1%). FIG. 2A represents the proportion of Pax7+ cells and FIG. 2B represents the proportion of MyoD+ cells. These data demonstrate that Pyridoxine promotes Muscle Stem Cell function by increasing the proportion of differentiating (MyoD+) cells in a dose dependent manner.

FIG. 3 represents the effect of nicotinamide and pyridoxine alone or combined on MyoD+ cells (from donor 3). For each condition, the number of MyoD+ cells was normalized to the number of MyoD+ cells in the control condition (DMSO 1%). FIG. 3A represents the number of MyoD+ cells normalized to the control condition. FIG. 3B represents the increase in MyoD+ cell number compared to the control condition (DMSO 1%). These data show that the effect of the combination of Nicotinamide and Pyridoxine is greater than the sum of the individual effect of Nicotinamide and Pyridoxine, indicating a synergistic effect. Indeed, by applying a linear regression model (interaction term, p=0.05), we were able to observe a statistically significant synergistic effect between the nicotinamide and pyridoxine.

As a comparative experiment, combination of Nicotinamide (NAM) with vitamin B9 was measured similarly as above (see FIG. 4). Unlike pyridoxine (vitamin B6), vitamin B9, another member of the B vitamin complex, does not have any addictive nor synergistic effect when added in combination with Nicotinamide.

Additionally, FIG. 5 demonstrates that the ratio between Pyridoxine and Nicotinamide (ratio Vitamin B6/NAM) has a relevant impact on promoting muscle stem cell function.

Example 2 In Vivo Effect of the Combination of
Nicotinamide (NAM) and Pyridoxine (B6) on
Muscle Stem Cells Function Material and Methods In order to reproduce the physiological process of muscle regeneration that occurs in adult skeletal muscles in response to injury or disease, we performed an intramuscular injection of cardiotoxin into mouse hindlimb muscles. One week prior to the induction of the muscle injury, mice were given by oral gavage our compounds of interest (nicotinamide and pyridoxine at 200 and 4 mg/kg body weight, respectively) vs. water control. Mice were treated once a day until the end of the experiment. To evaluate the efficiency of the muscle regeneration, muscles that have been previously injured were harvested 5 days after the injury and cryosections were prepared. Several myogenic markers were then measured. Cryosections were stained for Pax7, Myogenin, laminin (to delineate myofibers) and embryonic Myosin Heavy Chain (to define the injured/regenerating area) expression using specific antibodies and counterstained with Hoechst 33342 to visualize cell nuclei. Early phase of expansion and subsequent phase of myogenic differentiation of Muscle Stem Cells were evaluated by counting the number of Pax7+ cells (FIG. 6A) and Myogenin+ cells (FIG. 6B).

Data are expressed as number of cells per arear of injured muscle, expressed as a fold change compared to the control condition.

Results

These data demonstrate that a combination of Nicotinamide and Pyridoxine promotes Muscle Stem Cell function by increasing the number of both amplifying (Pax7+) and differentiating (MyoD+) cells in an in vivo preclinical model of muscle repair/regeneration (FIG. 6).

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

Example 3 Effect of the Combination of
Nicotinamide (NAM) and Pyridoxine (B6) on
Muscle Stem Cells Isolated at Different Ages after
Birth Material and Methods Muscle stem cells were isolated from hindlimb muscle of mice of different age: postnatal (4-day-old), juvenile (3-week-old) and adult (26-week-old) by flow cytometry after enzymatic digestion based on the following antigen signature: CD31⁻/CD11b⁻/CD45⁻/Sca1⁻/CD34⁺/Integrin α7⁺. Freshly isolated Muscle stem cells were then seeded in 384 well plates at a density of 1000 cells per well in growth medium (DMEM, 20% heat-inactivated Fetal Bovine Serum, 10% inactivated horse serum, 2.5 ng/ml bFGF (Invitrogen), 1% P/S+1% L+-Glutamine, 1% Na-pyruvate (Invitrogen)) and cultured for 4 days. For treatment, nicotinamide (at 10 mM) and pyridoxine (at the different ratios indicated in the FIG. 5) were directly added to the cultures at initial plating and medium were refresh every 2 days.

Cells were stained for Pax7 and MyoD expression using antibodies directed against Pax7 and MyoD and counterstained with Hoechst 33342 to visualize cell nuclei. Pax7+ cells are defined as cells that express Pax7 regardless of MyoD expression. MyoD+ cells are defined as cells that express MyoD regardless of Pax7 expression. Image acquisition was performed using the ImageXpress (Molecular Devices) platform. Custom module analysis based on Multi-Wavelength Cell Scoring of the MetaXpress software was used for quantification.

*, , *, **** indicates difference from the control, One-way ANOVA, with $p<0.05$, $p<0.01$, $p<0.001$, $p<0.0001$, respectively. Data are presented as Mean+/− SEM.

Results

For each age group, postnatal (4-day-old), juvenile (3-week-old) and adult (26-week-old), the total number of Pax7+ or MyoD+ cells in the conditions treated with NAM/B6 was normalized to the number of cells in the respective control conditions and expressed as a fold change compared to the control condition (DMSO 1%). FIG. 7A represents the number of Pax7+ cells and FIG. 7B represents the number of MyoD+ cells.

These data demonstrate that the combination of Nicotinamide and pyridoxine promotes Muscle Stem Cell function by increasing both amplifying (Pax7+) and differentiating (MyoD+) cells at a greater extend for Muscle Stem cells isolated from young animals (4-days and 3-week-old mice, which in humans corresponds to the infant and child stages, respectively) compared to adult animals (26-week-old mice). Overall, these results mean that, unexpectedly, the combination of NAM/B6 has a greater efficacy on Muscle Stem Cell function in early postnatal and juvenile individuals compared to adults.

The invention claimed is:

1. A method for promoting muscle growth and/or increasing muscle function and/or muscle mass in an infant, a young child, or a child in need thereof, the method comprising administering to the infant, young child, or child a composition comprising a combination of Vitamin B6 and Nicotinamide in a therapeutically effective amount.

2. The method according to claim 1, wherein promotion of muscle growth is achieved by increasing muscle function and/or muscle mass.

3. The method according to claim 1, wherein the vitamin B6 is administered in an amount of 1.0-200 mg vitamin B6 per day.

4. The method according to claim 1, wherein the Nicotinamide is administered in an amount of about 0.001 mg/day to about 2000 mg/day.

5. The method according to claim 1, wherein the Vitamin B6 and Nicotinamide are present in the composition in a ratio of from about 1:100 to about 1:9.

6. The method according to claim 1, wherein the Vitamin B6 and Nicotinamide are present in the composition in a ratio of from about 1:45 to about 1:30.

7. The method according to claim 1, wherein the composition is in a form selected from the group consisting of an oral nutritional composition, an infant formula, a follow up formula, a nutritional supplement, an oral nutritional supplement, a medical food, a food supplement, a food product, and a food for special medical purpose (FSMP).

8. The method according to claim 1, wherein the composition is in a form selected from the group consisting of a solid powder, a powdered stick, a capsule and a solution.

9. The method according to claim 1, wherein the administering of the composition promotes muscle growth in the subject.

10. The method according to claim 1, wherein the composition is a food product further comprising a component selected from the group consisting of protein, carbohydrate, fat and mixtures thereof.

11. The method according to claim 1, wherein Vitamin B6 is pyridoxine.

12. A method for promoting muscle growth and/or increasing muscle function and/or muscle mass in an infant, a young child, or a child in need thereof, the method comprising administering to the infant, young child, or child (i) a first composition comprising Vitamin B6 and (ii) a second composition comprising Nicotinamide.

13. The method according to claim 12, wherein the first composition is administered to provide 1.0-200 mg of the vitamin B6 per day.

14. The method according to claim 12, wherein the second composition is administered to provide about 0.001 mg-about 2000 mg of the Nicotinamide per day.

15. The method according to claim 12, wherein the first and second compositions are administered to provide the Vitamin B6 and the Nicotinamide in a ratio of from about 1:100 to about 1:9.

16. The method according to claim 12, wherein the first and second compositions are administered to provide the Vitamin B6 and the Nicotinamide in a ratio of from about 1:45 to about 1:30.

* * * * *